United States Patent [19]

Laversanne et al.

[11] Patent Number: 5,788,975
[45] Date of Patent: Aug. 4, 1998

[54] IMPROVING THE LASTING PROPERTIES OF AN ODOR BY ENCAPSULATING AN ODORIFEROUS INGREDIENT

[75] Inventors: René Laversanne, Pessac; Didier Roux, Merignac, both of France

[73] Assignee: Capsulis, Pessac, France

[21] Appl. No.: 682,578

[22] PCT Filed: Jan. 20, 1995

[86] PCT No.: PCT/FR95/00064

§ 371 Date: Jul. 22, 1996

§ 102(e) Date: Jul. 22, 1996

[87] PCT Pub. No.: WO95/19707

PCT Pub. Date: Jul. 27, 1995

[51] Int. Cl.$^6$ .............. B01J 13/06; A61K 9/50; A61K 9/52

[52] U.S. Cl. .............. 424/417; 424/490; 514/919

[58] Field of Search ................ 514/919; 424/409, 424/417, 490

[56] References Cited

U.S. PATENT DOCUMENTS

| 4,808,408 | 2/1989 | Baker et al. ............ 424/408 |
| 4,822,614 | 4/1989 | Rodero et al. ........... 514/919 |

FOREIGN PATENT DOCUMENTS

| 0224457 | 3/1987 | European Pat. Off. . |
| 0279328 | 8/1988 | European Pat. Off. . |
| 0307723 | 3/1989 | European Pat. Off. . |
| 0388239 | 9/1990 | European Pat. Off. . |
| 0463962 | 1/1992 | European Pat. Off. . |
| 2233095 | 1/1975 | France . |
| 2 689 418 | 10/1993 | France . |
| 03146600 | 6/1991 | Japan . |
| 85 05009 | 11/1985 | WIPO . |
| 90 10436 | 9/1990 | WIPO . |
| 93 19735 | 10/1993 | WIPO . |

OTHER PUBLICATIONS

"ANPP", B. Videau and S. Meghir, Dec. 1990, pp. 371–383.

*Primary Examiner*—Peter F. Kulkosky
*Attorney, Agent, or Firm*—Merchant, Gould, Smith, Edell, Welter & Schmidt

[57] ABSTRACT

The invention relates to an odoriferous composition containing a dispersion of microcapsules consisting of at least one surfactant with an odoriferous ingredient encapsulated therein.

A method for preparing said compositions and their use for giving off a scent for repelling animals are also disclosed.

28 Claims, No Drawings

IMPROVING THE LASTING PROPERTIES OF AN ODOR BY ENCAPSULATING AN ODORIFEROUS INGREDIENT

The present invention relates to a method for improving the lasting properties of an odour. More precisely, it relates to odoriferous compositions with improved lasting properties as well as to methods for preparing them and their mode of use.

Odoriferous products or mixtures within the meaning of the invention are understood to mean all products perceived as such by man or animals. Thus, the invention relates equally well to the domain of perfumes and products including an odoriferous composition or ingredient of which it is desired to prolong and control the pleasant olfactory effect and to that of repellants, in particular repellants for animals, where it is of interest to have available substances which are effective for a period of time which is as long as possible. It also concerns the domain of pheromones which are substances specifically sensed by certain animals and of which the effect on them is therefore assimilable to that of an odour.

Repellants for animals are formulations of products of which the odour repels the animals. Among known products having this effect, extracts of mustard are the most used. Commercial formulations present the drawback of having an effect very limited in time, and therefore require very frequent applications to ensure permanent efficacy (daily application).

It is known that, in the domain of plant protective formulations but also in that of odoriferous compositions, one often resorts to mixtures of active compounds and additives having for a role to ensure arrangement of the active products. Very often, the active product is a molecule or a mixture of hydrophobic molecules. For obvious reasons of facility of use, it is very useful to formulate the active product so as to render it dispersible or soluble in an aqueous medium. Among the methods enabling such an object to be attained, the use of surfactants often allows a good dispersibility and therefore facilitates use of the active ingredient.

One of the characteristics often sought in such formulations is the lasting property of the active ingredient. One manner of obtaining it often consists in using an excess of compounds. Other methods have been used, in particualr in the plant protection domain such as encapsulation by polymer (of coacervation type for example: cf. for example ANPP Second International Conference on Agricultural Pests "The microencapsulation of plant protection products", V. VIDEAU and S. MEGHIR, page 371). These techniques generally present the drawback of being difficult and expensive to carry out. Moreover, the release of the active ingredient from the capsule is not well controlled and is generally governed by the destruction of the capsule, either chemically (hydrolysis), or mechanically.

Independently of the dispersing effect, the surface-active molecules make it possible in certain cases to protect and vectorize then release in controlled manner active molecules, by using microcapsules formed by a supramolecular association of the surface-active molecules. The most current example is that of liposomes used in cosmetics and in the biomedical domain. These liposomes correspond to an arrangement in vesicles (uni-lamellar or multi-lamellar) of dimensions included between some hundreds of Angströms and several microns. These vesicles are, in the case of liposomes, obtained from phospholipidic molecules (extracted for example from soja or egg). These liposomes are capable of encapsulating lipophilic or even hydrophilic active molecules and thus of performing the functions of vectorization and release envisaged.

French Patent FR 2 689 418 describes a method which, thanks to resorting to a step of shearing of a lamellar crystal-liquid phase, makes it possible to prepare microcapsules of controlled size, not only from lipidic surfactants capable of forming liposomes but also from different anionic or non-ionic surfactants and proposes encapsulation of substances, particularly biological ones, in these capsules.

European Patent Application EP 0 388 239 describes the use of a medium containing a structured surfactant, forming microcapsules to prepare a suspension of an agrochemical product insoluble or very sparingly soluble in the medium. In such a process, the active agrochemical product is not included inside the microcapsules but is in suspension in the medium surrounding these microcapsules.

Applicants have now discoverd that a means for obtaining a controlled olfactory effect and in particular to obtain increased lasting properties of an odour consisted in encapsulating a product or an odoriferous composition in microcapsules made of surface-active molecules.

Although in the present specification the terms "encapsulation" and "microcapsule" are used, these terms have meanings substantially different from those that they have when it is question of microcapsules of polymeric type of the prior art, this being due to the particular structure of the entities obtained according to the invention.

In fact, according to the invention, it is the surfactant(s) which constitute(s) the membranes of the microcapsules.

The microcapsules according to the invention are more precisely in multi-lamellar form, i.e. they are constituted by concentric lamellae which give them a structure of the onion type.

The product of the odoriferous composition is included within the microcapsule itself, generally in its membranes, if necessary, if it is purely hydrophilic, in the interstitial water included within the microscapsule. However, it always forms an integral part of the microcapsule.

Such an encapsulation makes it possible to ensure the functions of dispersibility in aqueous medium, of vectorization and of controlled release of the active mixture responsible for the odour.

In particular, it improves the lasting properties of the odour, which proves particularly useful both when it is question of perfuming an atmosphere, a surface, linen or a fabric, a person or an object, and of spreading a repellant odour particularly desired in the case of repellants for animals.

In this latter case, more particularly, the invention makes it possible to formulate an active ingredient acting as animal repellant in microcapsules and to obtain, thanks to this encapsulation, a prolonged activity of the active product which may exceed several weeks after the treatment of ground by an aqueous dispersion of this formulation.

A first advantage of the invention comes from the fact that, after positioning the product formulated, the regular leakage of the capsules ensures a slow availability of the active ingredient.

Another advantage of the invention resides in the fact that manufacture of the microcapsules is obtained directly by mixing the active ingredient and a judiciously selected mixture of surfactants.

Another advantage of the invention resides in the fact that the use of the surfactants procures a very good dispersibility for the formulation, which may be used in liquid form, in aqueous dispersion. This aspect is particularly advantageous when hydrophobic molecules are in question or those non-soluble in water which may be dispersed thanks to the invention without having to resort to an organic solvent.

The mixture is advantageously in the form of a milk, very easily spreadable with the conventional apparatus such as spray or watering can, which constitutes another undeniable advantage of the invention.

Thus, according to a first aspect, the invention relates to novel odoriferous compositions particularly interesting for their character of lasting properties but also for their physical shape.

According to a second aspect, the invention concerns a method for preparing these compositions.

According to a third aspect, the invention relates to uses of these compositions in particular to perfume directly, for example by aspersion, an atmosphere, a surface, a person or an object when the active ingredient is a pleasant perfume. The compositions of the invention may also be used as additives in washing, detergent or cosmetic products, with a view to improving lasting properties of the perfume that they confer.

The compositions of the invention may also be used as repellant agents for animals, for example for domestic animals or birds when an active ingredient ill-smelling for them is chosen.

Finally, according to a last aspect, the invention relates to a method for controlling the diffusion of an odour and in particular to improve the lasting properties thereof.

According to an essential characteristic of its first aspect, the invention concerns an odoriferous composition containing at least one odoriferous agent and at least one surface-active agent, in which said odoriferous agent is encapsulated in microcapsules constituted by a multi-lamellar arrangement of concentric bilayers of surfactant(s) separated by an aqueous medium called interstitial water, said odoriferous agent being included in the membranes of said microcapsules when it is hydrophobic and/or in the interstitial water of said microcapsules when it is hydrophilic.

The microcapsules contained in the compositions of the invention advantageously present dimensions included between 0.1 and 100 µm, preferably between 0.2 and 10 µm.

These microcapsules may be observed with an optical microscope. They advantageously present a size, preferably of the order of a micron. Due to this small size, the microcapsules are subjected to Brownian agitation and do not undergo, or undergo only little, decantation or creaming.

The surface-active agent or agents contained in the composition of the invention may be of any type of surface-active agents capable of forming microcapsules.

It may be question, in particular, of lipidic products, in particular of products capable of forming liposomes.

However, the surface-active agents will preferably be selected from the non-ionic, anionic, cationic or amphoteric surfactants.

These surface-active agents are advantageously selected from the saturated or unsaturated fatty acid derivatives, preferably the fatty acid derivatives with carbon chain (s) included between $C_6$ and $C_{20}$ containing zero, one or several unsaturations.

The polar head of these surface-active agents may be ionic of anionic type; it will be question for example of an ethoxylate, sulfate or sulfonate group.

The polar head may also be cationic; it will be question for example of a quaternary ammonium, or of an amine.

It may also be amphoteric. This is the case, for example, of betaïne.

The head may also be non-ionic; it may be question, for example, of an ester or of an ethoxylated ether. By way of example of such products, the esters of glycerol and of sorbitol, ethoxylated or not, will be cited.

The polar head may also present several parts, combining a non-polar part, such as ethylene oxide segments, and an ionic, anionic or cationic part.

The surface-active agent(s) will advantageously be present in the composition at a rate of 0.5 to 500 g/l, preferably 1 to 200 g/l, and preferably still, from 5 to 100 g/l.

For the preparation of the compositions according to the invention, one advantageously resorts to a mixture of surfactants selected either from the same class mentioned above, or from different classes.

By way of mixture of surfactants particularly useful according to the invention, mention will be made of the mixture of sorbitol oleate and stearate and their mixtures with ethoxylated sorbitol ethers or with ammonium salts or salts of amines.

Another particularly useful surface-active mixture according to the invention is constituted by a mixture of fatty alcohol and a surfactant of ionic type. Such a mixture may in particular be constituted by dodecanol and dodecylsulfate of sodium.

The odoriferous agent may, as set forth hereinbefore, either be a perfume, for example an essence or a perfuming composition. In that case, the microcapsules may be used either in the pure state in the form of cream, in order to dispense the perfume in the atmosphere over a long period of time, or dispersed in an aqueous phase, in order to be atomized on the ground or a support, or in order to impregnate a porous support. In other applications of the invention, the capsules may advantageously be used either for dispersing the perfume, for example in bases of detergent products, floor-cleaning agent, washing powder, softener, in order to give lasting properties to the perfuming action of these products, or introduced in a cosmetic or dermocosmetic preparation, for example a cream, an emulsion, a gel, a shampoo, in order to benefit both from the advantage of dispersibility of the microcapsules in this type of medium and from the long-lasting effect of the odour.

The odoriferous agent may also be a bad smell, whether it be perceived as such by man or whether it be specifically repellant for certain animals, for example dogs or cats, harmful wild animals, insects or birds. In that case, the composition will be intended to be used as repellant agent for these animals, in order to prevent the damage or nuisance that they may cause.

The odoriferous agent may also be a compound of the class of pheromones, natural or artificial, used for controlling the behaviour or population of certain animals, mammals or insects. In this case, the composition will be intended to be used either in traps, in order to attract the animals, or to be spread over the zones to be protected.

Should it be desired to keep the animals at a distance, the active ingredient is advantageously selected from the chemical compounds presenting a strong smell, principally in the family of thiols, amines or ketones. For this application, essential oils or mixtures of these oils which are known to have a repellant action on the animals concerned, may also be used.

This active ingredient may be liquid or solid at ambient temperature.

This active ingredient will preferably be chosen from tertiary amines and cyclic amines which are perfectly suitable.

By way of examples of other products particularly adapted for this application as repellant for animals, mention will be made, for dogs and cats, of pyridine, 2-undecanone or 5-methyl-2-hexanone and for mosquitoes, diethyl meta toluiamide (DEET) or repellant 3535 of Merck. By way of example of natural essences particularly adapted as repellants, mention will be made among the natural essences which are known to have a repellant action for cats, essence of rue, for mosquitoes, essence of citronella or Neem-Oil extract, for spiders, extracts of sweet chestnuts or horse chestnuts. The concentration of the active ingredient is advantageously included between 0.01 and 250 g/l, preferably between 0.1 and 100 g/l, in the case of products repellant for animals.

Where the compositions are used as perfume, the minimum content may of course be clearly lower, the only imperative being that this odour be perceptible.

A particularly interesting composition according to the invention usable as repellant, particularly for dogs and cats, comprises as surface-active agent a mixture of oleate and stearate of sorbitol and, as odoriferous agent, pyridine.

According to a second aspect, the invention concerns a method for preparing the compositions described hereinabove.

The method of preparation of the invention consists in preparing a crystal-liquid phase or a suspension of crystal-liquid phase in water, in solubilizing the active molecules and in provoking a re-arrangement in the form of microcapsules of the bilayers of surfactant.

This re-arrangement may, according to a first variant, be effected spontaneously by addition of water.

Re-arrangements of the surfactant of this type are described in particular in patent application Ser. No. EP 0 388 239 which differs from the present invention essentially by the nature of the active substance and by the fact that it is soluble in the case of this Application neither in the membranes of the microcapsules nor in the interstitial water, which leads in that case to obtaining a suspension of active product in a mixture containing microcapsules and not, as in the case of the present invention, to a dispersion of microcapsules containing in their core the active product which is trapped either in the membrane of the microcapsules or in the interstitial water.

According to another variant of the invention, the re-arrangement of the bilayers to form microscapsules is provoked mechanically, by shearing.

Such a process of formulation of the microcapsules involving a step of shearing is described in French Patent Application FR 2 689 418.

A method for preparing the compositions of the invention is described hereinbelow.

More precisely, the microcapsules are prepared from a crystal-liquid phase (lamellar phase for example) or from a suspension of crystal-liquid phase in water, in which the active molecules are solubilized. From this crystal-liquid phase, either the microcapsules form spontaneously during addition of water, or it is necessary to apply a mechanical method such as the one described in Patent FR 2 689 418 introduced here by reference. It is possible to manufacture these microcapsules from very varied surfactants and not only from phospholipidic molecules.

The capsules correspond to a multi-lamellar arrangement of bilayers of surfactants separated by an aqueous medium. The active product is incorporated either in the membrane if it is lipophilic or in the interstitial water if it is hydrophilic. In the case of the product being partially miscible in an aqueous and organic medium, it is distributed between the membrane and the trapped water. Depending on the surfactant or the mixture of surfactants used, the structure of the membrane is fluid or in the solid state (gel).

A fluid membrane is characterizd in that the surfactant molecules which constitute it are free to move in the surface defined by the bilayer (two-dimensional liquid or fluid). A gel membrane is defined by the molecules which constitute it forming a solid bidimensional network. It is possible to pass the membranes from the gel state to that of fluid by increasing the temperature (gel/liquid transition). The properties of controlled release are very different depending on whether the membrane is in a fluid or gel state. In particular in the case of the gel state, the leakage of the active ingredient is substantially slowed down with respect to the fluid state. The case will therefore preferably be chosen where the membrane is in the gel state to formulate products with very long retention time.

The man skilled in the art knows that the choice of the surfactants and their proportions are primordial, as they perform the role both of encapsulant for the active ingredient and of dispersant for the formulation. It is in fact this choice which makes it possible to prepare microcapsules and which determines the nature of the membrane which composes them (gel or liquid). The capsules may be made from one type or from several types of surface-active molecules. In the case of a mixture, the proportion of this mixture makes it possible to regulate the temperature of transition of the surfactant membrane (gel/liquid transition) and therefore to regulate the encapsulating properties of the microcapsules.

Other compounds conventionally used to that end may be added to improve fluidity of the formulation or its dispersibility.

In order to prepare the compositions of the invention, one advantageously proceeds as follows: in a first step, a mixture is prepared, containing the assembly of the or each surfactant, the or each active product and the minimum of water necessary to obtain a homogeneous phase. If necessary, this mixture may be made at high temperature (from 10° to 120° C., preferably between 20° and 70° C.). This phase is generally but not compulsorily a lamellar crystal-liquid phase, this crystal-liquid phase being able to exist only at temperature lower than that used for solubilizing all the constituents. In that case, it is preferable to lower the temperature of the mixture before effecting the following step. The presence of a lamellar crystal-liquid phase is easily characterized by an observation under polarizing microscope (observation of the characteristic texture of lyotropic lamellar phase), or by diffraction of the X rays which in addition gives the characteristic distance between the membranes of which the stack forms the lamellar phase. The viscosity of this phase is generally relatively high (from $10^{-2}$ to 10 Pa.s).

In the following step, the initial mixture is diluted with pure water with stirring until the optimum concentration of active products is obtained. The method described in Pat. No. FR 2 689 418 may independently but without obligation be used in order to obtain a compact assembly of spherulites of controlled sizes. In all cases, the product may be prepared in concentrated form then diluted to the optimum concentration of use. The microcapsules formed may be observed by optical microscopy directly under a microscope. Their size may be measured in diluted solution by dynamic diffusion of light.

As has been seen previously, the invention also concerns, in accordance with a third aspect, the use of the compositions described previously or obtained in accordance with the method described previously to perfume an atmosphere, a surface or an object, linen, a person, in the case of the active agent being a substance or a mixture of pleasant perfume, for example an extract, a defined compound or a perfuming base.

According to another aspect, it concerns the use of a composition according to the invention in which the active agent is known for its strong odour or its repellant action on certain animals such as animal repellant agent. This active ingredient may be a chemical agent or a natural essence or a mixture of essences.

Finally, according to a last aspect, the invention concerns, as has been seen hereinabove, a method for controlling the diffusion of a characteristic odour of a product or a mixture and in particular for increasing the lasting properties thereof, consisting in diffusing a composition as defined previously over a surface, in an atmosphere, on an object or via a washing product, on linen.

The following examples are given purely by way of illustration of the invention.

EXAMPLE 1

50 g of pyridine, 15 g of sorbitol oleate (Sorban AO marketed by Witco) and 20 g of sorbitol stearate (Sorban AST marketed by Witco) are mixed with stirring. This mixture may be made at 60° C. in order to accelerate dissolution.

When the mixture is dissolved, 915 g of water are added with strong stirring to obtain 1 l of milky compound which may be used directly.

This composition spread over a pavement at a rate of 1 g of active product (pyridine) per m² leads to its repellant effect with respect to dogs and cats lasting for 15 days.

Observation of the composition under contrasting phase microscopy shows that it is constituted by a dispersion of spherules whose dimensions are included between 1 and 2 μm.

EXAMPLE 2

The pyridine and the surfactants are mixed as in Example 1 but heating towards 50° C.

915 g of water are added in the mixture at 50° C. with moderate stirring and the mixture is allowed to cool slowly, maintaining stirring.

A composition is obtained, whose structure is identical to that of Example 1 and which presents an effect of lasting properties of the same order.

EXAMPLE 3

The pyridine and the surfactants are mixed hot as in Example 2. In the hot mixture, 115 g of water are slowly added with stirring, the mixture is allowed to cool with stirring. A fluid cream is obtained, usable after dilution in water to obtain a final product with the same concentration as that of Example 1.

The same effects are obtained concerning the lasting properties of the effect.

This composition spread over a pavement at a rate of 1 g of active product (pyridine) per m² leads to the repellant effect with regard to dogs and cats lasting more than 3 weeks.

Observation of the composition under contrasting phase microscopy shows that it is constituted by a dispersion of spherules with dimensions included between 1 and 2 μm.

The effect of slowing down the leakage of the pyridine may be demonstrated by measuring the quantity of pyridine remaining in samples previously weighed and evaporated in an atmosphere controlled in temperature and hygrometry for increasing times of some minutes to some weeks. The quantity of pyridine may be measured by gaseous phase chromatography after extraction of the sample evaporated by alcohol. The line of the curve giving the mass of pyridine remaining a function of time, for a sample of the product according to this Example and for a solution of pyridine in water, clearly shows that, in the case of the product according to this Example, the long-time evaporation kinetics of the pyridine are effected with a time constant of the order of 10 days, instead of 2 hrs. for pyridine in water.

EXAMPLE 4

A lamellar phase is prepared by heating to 60° C. a mixture of 10 g of stearyl polysorbate (Montanox 60, SEPPIC), 42 g of sorbitol stearate, 35 g of water and 12 g of 5-methyl-2-hexanone, then allowing the mixture to cool with stirring. The cream obtained is dispersed in water to obtain a dispersion of microspheres titrated at 2% in ketone.

This dispersion may be used as dog repellant under the same conditions as the product of Example 3, with the advantage of having a less strong odour during application.

EXAMPLE 5

The 5-methyl-2-hexanone of Example 4 may be replaced either by 2-undecanone, or by oil of rue of which the 2-undecanone is one of the odoriferous ingredients. The mode of preparation is unchanged with respect to Example 4.

This product is particularly efficient with regard to cats. Tested under the same conditions as in Example 3, it shows an efficiency greater than 15 days.

EXAMPLE 6

A concentrated dispersion of multi-lamellar microspheres is obtained by heating 10 g of stearyl polysorbate (Tween 60, ICI), 14 g of sorbitan stearate (span 60, ICI), 63 g of water and 13 g of extract of horse chestnut (Flachsmann) with stirring up to 60° C., then allowing the mixture to cool, maintaining stirring.

The bi-refringent microspheres are clearly visible by observation with an optical microscope.

This disperson may be diluted to obtain a product titrated at 4% of horse chestnut extract. This product, sprayed on floors, walls, beams, etc., prevents the arrival of spiders for several weeks, thanks to the lasting effect thus given to the well known repellant action of the essences of sweet chestnuts or horse chestnuts with regard to these animals.

EXAMPLE 7

Diethyl meta toluiamide (DEET) may be incorporated in the same manner in multi-lamellar microspheres. A mixture of 10 g of sorbitan stearate, 10 g of stearyl polysorbate, 15 g of DEET and 65 g of water is heated with stirring up to 60° C., then cooled with stirring. The mixture thus obtained is formed by a dispersion of birefringent microspheres and does not show the presence of emulsified droplets of DEET.

DEET may be considered as a repellant odour for insects, in particular for mosquitoes. The preceding product may be tested directly in its concentrated form which has the appearance and texture of a cosmetic cream.

The tests effected on mice coated with the above composition and placed in the presence of *Aedes Aegypti* mosquitoes in comparison with the same tests made with DEET in alcoholic solution (isopropanol) at the same concentration and with a commercial product (Ultrathon) show lasting properties increased by more than an hour when the product is incorporated in the microspheres.

EXAMPLE 8

Encapsulation of essence of lavender

Essence of lavender is encapsulated in the microscapules of surfactants in gel phase.

a) Preparation of the mixture

A mixture of 12% by weight of sodium dodecylsulfate, 18% of dodecanol and 1% essence of lavender is mixed with 69% of water. A lamellar crystal-liquid phase in gel phase is obtained which may be characterized by optical microscopy (texture) or/and by X-ray diffraction. The membranes in gel phase at ambient temperature are transformed into liquid phase at a temperature of about 40° C., which transition may be observed either by optical microscopy or by X-ray diffraction.

b) Formation of the microcapsules

To prepare the concentrated phase of microcapsules, the method described in Patent FR 2 689 418 is used (application of a homogeneous shear of $20s^{-1}$), at a temperature greater than the gel/liquid transition temperature. T=50° C. has been chosen in the Example described. The homogeneous shear is applied for 5 hrs., then the cream thus formed is recovered at ambient temperature. This cream is composed of a stack of microcapsules of the order of 0.4 µm diameter. The size may be measured by dynamic diffusion of the light after dispersion of the microcapsules in a large excess of water.

In the above formulation, the microcapsules exist spontaneously without the obligation of applying a shear, while the use of the method described in Pat. No. FR 2 689 418 makes it possible to obtain a better quality of the microcapsules and a better control of their sizes. This ensures a better dispersibility of this cream in water.

Whether the shear is applied or not, the following steps are similar.

c) Preparation of a dilute solution of microcapsules

This cream may be dispersed by stirring in an excess of water. In this way, a suspension of microcapsules containing essence of lavender is obtained.

d) Lasting properties of the odour

To test the long-lasting effect, two pieces of fabric are respectively immersed in a $1/1000$ solution of capsules corresponding to $0.01/1000$ of essence of lavender and in a $0.01/1000$ solution of pure essence of lavender (non-encapsulated) in a dilute alcoholic mixture (in order to ensure complete dissolution of the essence of lavender). Once dried, the odour of lavender which impregnates the fabric persists after one day (24 hours) for the fabric immersed in the solution of microcapsules, while it disappears after 2 to 3 hrs. in the case of the dilute alcoholic solution.

Another manner of testing the long lasting effect consists in dispersing in water, in several bottles which may be hermetically closed, a quantity of microcapsules such that the concentration of essence of lavender is about 5 per 1000. The bottles are then opened for a period of 10 hrs., 20 hrs., 48 hrs., etc.; then closed again. The odour is then compared with that of an essence of lavender simply dissolved in water, at the same concentration and left open under the same conditions. Two phenomena are observed. After 24 hrs., the non-encapsulated controls no longer smell, while the lavender perfume is still present in the encapsulated samples beyond 48 hrs. Moreover, while for the non-encapsulated controls, the perfume is quickly denatured, allowing only the body hints to appear in a few hours, the microencapsulated perfume has kept its bouquet intact even after 48 hrs. evaporation.

EXAMPLE 9

Microencapsulated perfume for textile softener

A mixture composed (by weight) of 5 g of Tween 60 (of the firm ICI), 40 g of span 60 (of the firm ICI), 5 g of dialkyl-dimethyl ammonium on a base of hydrogenated tallow (Noramium M2SH of the firm CECA) and 40 g of water, is melted with stirring at 60° C. When the temperature is less than 40° C., 10 g of a perfuming base for textile softener (for example Vansyn N●1 by Payan-Bertrand, Grasse) are introduced and stirring is maintained until the temperature returns to ambient. A lamellar phase of fairly fluid characteristic texture is obtained. This may be dispersed directly in a softening base (for exmaple 15% of Dehyquart AU-56 of the firm HENKEL in water) to obtain a concentration of perfume of 0.5 to 1%.

The tests of lasting properties may be effected either by hand by soaking in water to which the linen softening agent has been added (at a rate of 50 ml for 10 l of water), then drying in the air, or by washing in a machine and drying on a drier. The effect of long-lasting is very clear, the linen remaining perfumed for more than a week.

EXAMPLE 10

A long-lasting perfuming composition for floor cleaner may be obtained by incorporating in multilamellar microspheres a perfume with "pine" hints.

The microspheres are formed by a mixture of 4.6 g of stearyl polysorbate (Tween 60), 16.7 g of sorbitol stearate (span 60), 1.85 g of ethoxylated monoamine (noramox Cl5, CECA), 71.3 g of water and 5.5 g of "pine" perfume. After heating then cooling with stirring, a birefringent fluid cream is obtained which may be dispersed in a floor cleaning product.

The use of this product under the usual floor-cleaning conditions makes it possible to smell the "pine" perfume several hours after washing.

EXAMPLE 11

Microspheres containing the preceding "pine" perfume may be dispersed in water in order to obtain a super-odoriferous product intended to be used jointly with floor washing.

The lamellar phase is obtained by heating with stirring a mixture of 35 g of stearyl polysorbate (Tween 60), 5 g of sorbitol stearate (span 60), 5 g of dialkyl-dimethyl ammonium chloride on a base of hydrogenated tallow (Noramium M2SH, CECA), 35 g of water and 20 g of perfume.

After cooling with stirring, a thick birefringent cream is obtained which may be dispersed very easily in water for example to obtain a dispersion titrated at 1% of perfume.

This dispersion may be sprayed directly on the floor, before washing by hand or with a polishing machine. The odour of pine then remains perceptible in the room treated for more than a week, in particular on plastic floorings.

We claim:

1. An odoriferous composition for providing an extended olfactory effect from an odoriferous agent, comprising a plurality of microcapsules, the microcapsules comprising as an active odoriferous agent a volatile organic odoriferous compound that provides a desired odoriferous effect upon release from the microcapsules, the volatile organic odoriferous compound being selected from the group consisting of perfumes, repellents and pheromones, the microcapsules having a multi-lamellar structure defined by concentric layers of organic compound surfactant as membranes that are separated by aqueous interstitial layers, the volatile organic odoriferous compound being present in the aqueous interstitial layers when it is hydrophilic, the volatile organic odoriferous compound being present in the surfactant membrane when it is hydrophobic, the multi-lamellar microcapsules providing a controlled and extended release of the volatile organic odoriferous compound.

2. A method of providing controlled diffusion of an odoriferous product, comprising treating an object, a surface or an atmosphere for which an extended olfactory effect from an odoriferous agent is desired with:

an odoriferous composition comprising a plurality of microcapsules, the microcapsules comprising as an active odoriferous agent a volatile organic odoriferous compound that provides a desired odoriferous effect upon release from the microcapsules, the volatile organic odoriferous compound being selected from the group consisting of perfumes, repellents and pheromones, the microcapsules having a multi-lamellar structure defined by concentric layers of organic compound surfactant as membranes that are separated by aqueous interstitial layers, the volatile organic odoriferous compound being present in the aqueous interstitial layers when it is hydrophilic, the volatile organic odoriferous compound being present in the surfactant membrane when it is hydrophobic, the multi-lamellar microcapsules providing a controlled and extended release of the volatile organic odoriferous compound.

3. An odoriferous composition according to claim 1, wherein said microcapsules are manufactured by a process involving a step of preparing a liquid-crystal phase or a suspension of liquid-crystal phase containing said volatile organic compound and transforming said liquid-crystal phase into microcapsules by rearrangement of the bi-layers of surfactants.

4. Composition according to claim 1, characterized in that said microcapsules have dimensions between 0.1 and 100 μm.

5. Composition according to claim 1, characterized in that the composition contains a non-ionic, anionic, cationic or amphoteric surfactant, or a mixture of surfactants selected from the same class or not.

6. Composition according to claim 1, characterized in that the surfactant is a saturated or un- saturated fatty acid derivative.

7. Composition according to claim 3, characterized in that the fatty acid is a fatty acid with $C_6$ to $C_{20}$ carbon chains containing 0, 1 or several unsaturations.

8. Composition according to claim 1, characterized in that the microcapsules comprise at least one surfactant of ethoxylate, sulfate, sulfonate, ethoxylated ether or ester type.

9. Composition according to claim 1, characterized in that it contains 0.05 to 500 g/l of surfactant or mixture of surfactants.

10. Composition according to claim 1, characterized in that the surfactant is constituted by a mixture of sorbitol stearate and oleate or a mixture of these compounds with ethoxylated sorbitol ethers or salts of ammonium or of amines.

11. Composition according to claim 1, characterized in that the surfactant is constituted by a mixture of fatty alcohol and an ionic surfactant.

12. Composition according to claim 1, characterized in that the odoriferous agent is a perfume.

13. Composition according to claim 1, characterized in that the odoriferous agent is an ill-smelling product or sensed as such by animals, the compound being intended to be used as animal repellant agent.

14. Composition according to claim 13, characterized in that the odoriferous agent is a thiol, an amine, and a natural essence known for its repellant effect.

15. Composition according to claim 13, characterized in that the odoriferous product is at a concentration between 0.01 and 250 g/l.

16. Composition according to claim 1, characterized in that the odoriferous agent is a natural or synthetic pheromone.

17. Composition according to claim 1, characterized in that the surface-active agent is a mixture of sorbitol oleate and stearate and the odoriferous agent is pyridine.

18. A composition according to claim 4, wherein the dimensions are between 0.2 and 10 μm.

19. A composition according to claim 8, wherein the surfactant is selected from the group consisting of glycerol ester, optionally ethoxylated sorbitol ester, quaternary ammonium, amine and betaine surfactants.

20. A composition according to claim 11, wherein the mixture comprises dodeconal and dodecyl sulfate.

21. A composition according to claim 12, wherein the perfume is an essence or a perfuming composition.

22. A composition according to claim 11, wherein the odoriferous agent is selected from the group consisting of pyridine, 2-undecanone, 5-methyl-2-hexanone, diethyl meta toluimide, essence of rue, essence of citronella, extract of Neem Oil, extract of sweet chestnut and extract of horse chestnut.

23. A composition according to claim 12, wherein the concentration of the odoriferous agent is between 0.1 and 100 g/l.

24. A method according to claim 2, wherein the method provides a pleasing odor for an extended time, and the odoriferous agent is a perfume.

25. A method according to claim 2, wherein the method provides an animal repellent affect for an extended time, and the odoriferous agent is one that is sensed as unpleasant by the animal.

26. A method according to claim 24, wherein the composition according to claim 1 is applied to a human.

27. A method according to claim 26, wherein the composition according to claim 1 is applied to a human.

28. A method according to claim 24, wherein the composition according to claim 1 is applied to an article of clothing during laundering of the article of clothing.

* * * * *